(12) United States Patent
Buchanan et al.

(10) Patent No.: US 9,700,225 B2
(45) Date of Patent: *Jul. 11, 2017

(54) WEARABLE MEDICAL SYSTEM WITH STRETCH-CABLE ASSEMBLY

(71) Applicant: West Affum Holdings Corp., Grand Cayman (KY)

(72) Inventors: Robert Reuben Buchanan, Bothell, WA (US); David Peter Finch, Bothell, WA (US); Dallas Eugene Meeker, Kirkland, WA (US); Laura Marie Gustavson, Redmond, WA (US); Daniel James Finney, Woodinville, WA (US); Phillip Dewey Foshee, Jr., Woodinville, WA (US); Douglas Keith Medema, Everett, WA (US); Kenneth F. Cowan, Kirkland, WA (US); Karen Elizabeth McEwen, Kenmore, WA (US); Gregory T. Kavounas, Bellevue, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,588

(22) Filed: Jun. 24, 2016

(65) Prior Publication Data
US 2016/0302685 A1 Oct. 20, 2016

Related U.S. Application Data

(62) Division of application No. 14/510,081, filed on Oct. 8, 2014, now Pat. No. 9,402,988.

(Continued)

(51) Int. Cl.
*A61N 1/04* (2006.01)
*A61B 5/0428* (2006.01)
(Continued)

(52) U.S. Cl.
CPC ........ *A61B 5/04286* (2013.01); *A61B 5/0416* (2013.01); *A61B 5/04085* (2013.01);
(Continued)

(58) Field of Classification Search
None
See application file for complete search history.

(56) References Cited

U.S. PATENT DOCUMENTS 3,724,455 A 4/1973 Unger
4,583,524 A 4/1986 Hutchins
(Continued)

OTHER PUBLICATIONS

LifeVest Model 4000 Patient Manual, Zoll PN 20B0047 Rev B.
(Continued)

*Primary Examiner* — Brian T Gedeon
(74) *Attorney, Agent, or Firm* — Kavounas Patent Law Office, PLLC

(57) ABSTRACT

A Wearable Medical System includes a support structure that is configured to be worn by a person. The WMS also includes an electronics module, a cable assembly, and at least one electrode that can be configured to be coupled to the support structure. The cable assembly includes a base member and a cable coupled to the base member. The support structure can be dimensioned relative to the person's body to be worn with tension, and be resiliently stretched under the tension. The stretching of the support structure can stretch the base member of the cable assembly, thus increasing the effective length of the cable, while reducing or even eliminating slack in the cable.

35 Claims, 9 Drawing Sheets

Related U.S. Application Data

(60) Provisional application No. 61/989,464, filed on May 6, 2014.

(51) Int. Cl.
    *H04B 1/3827*     (2015.01)
    *A61B 5/0408*     (2006.01)
    *A61B 5/0416*     (2006.01)
    *A61B 5/00*     (2006.01)

(52) U.S. Cl.
    CPC ............ *A61B 5/6831* (2013.01); *A61N 1/046* (2013.01); *A61N 1/0484* (2013.01); *A61N 1/0492* (2013.01); *H04B 1/385* (2013.01); *H04B 1/3827* (2013.01); *A61B 2562/164* (2013.01); *A61B 2562/222* (2013.01)

(56) References Cited

U.S. PATENT DOCUMENTS

| | | |
|---|---|---|
| 4,619,265 A | 10/1986 | Morgan et al. |
| 5,078,134 A | 1/1992 | Heilman et al. |
| 5,228,449 A | 7/1993 | Christ et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 6,047,203 A | 4/2000 | Sackner et al. |
| 6,065,154 A | 5/2000 | Hulings et al. |
| 6,108,197 A | 8/2000 | Janik |
| 6,201,992 B1 | 3/2001 | Freeman |
| 6,263,238 B1 | 7/2001 | Brewer et al. |
| 6,287,328 B1 | 9/2001 | Snyder et al. |
| 6,319,011 B1 | 11/2001 | Motti et al. |
| 6,334,070 B1 | 12/2001 | Nova et al. |
| 6,356,785 B1 | 3/2002 | Snyder |
| 6,529,875 B1 | 3/2003 | Nakajima |
| 7,559,902 B2 | 7/2009 | Ting et al. |
| 7,865,238 B2 | 1/2011 | Brink |
| 7,870,761 B2 | 1/2011 | Valentine et al. |
| 8,140,154 B2 | 3/2012 | Donnelly et al. |
| 8,644,925 B2 | 2/2014 | Volpe et al. |
| 8,965,500 B2 | 2/2015 | Macho et al. |
| 9,008,801 B2 | 4/2015 | Kaib et al. |
| 9,131,901 B2 | 9/2015 | Volpe et al. |
| 9,132,267 B2 | 9/2015 | Kaib |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2011/0288605 A1 | 11/2011 | Kaib et al. |
| 2012/0144551 A1 | 6/2012 | Guldalian |
| 2012/0158075 A1 | 6/2012 | Kaib et al. |
| 2012/0265265 A1 | 10/2012 | Razavi et al. |
| 2014/0378812 A1 | 12/2014 | Saroka et al. |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

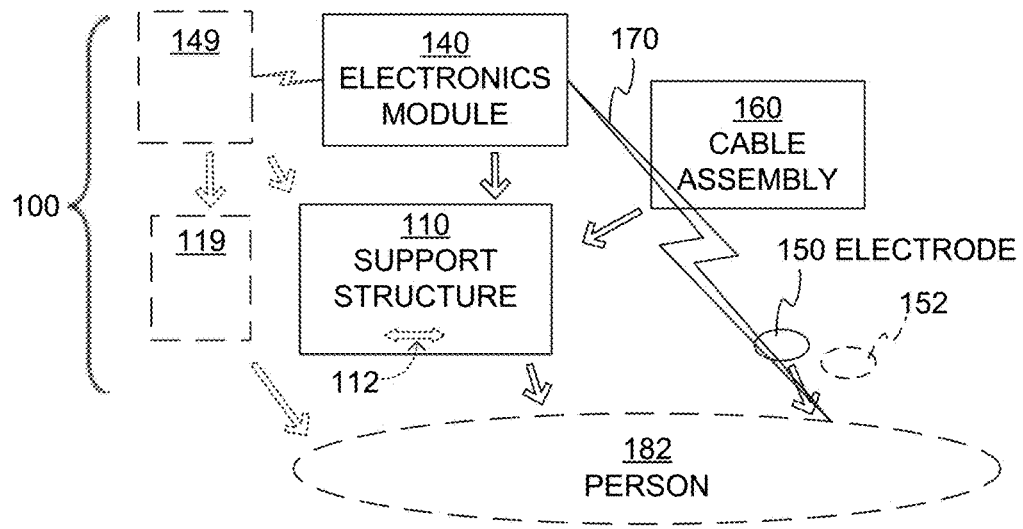
FIG. 1 COMPONENTS OF WEARABLE MEDICAL SYSTEM
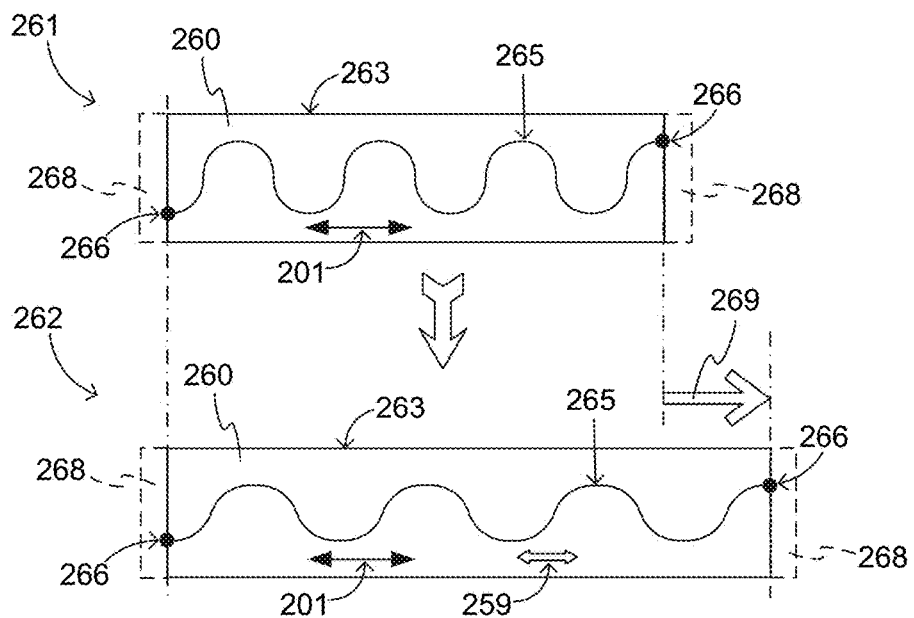
FIG. 2 CABLE ASSEMBLY

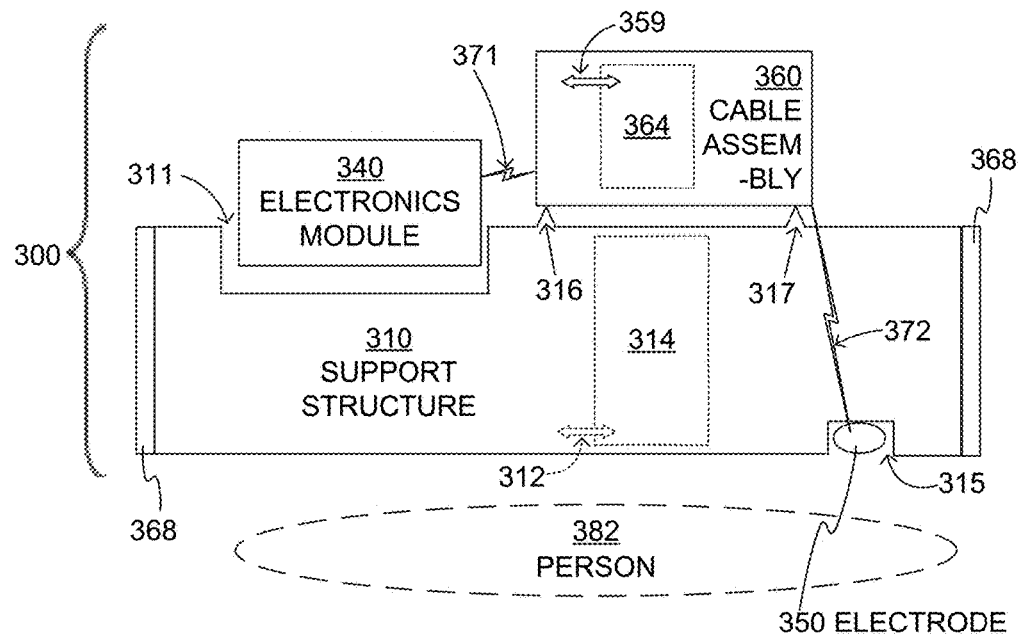
FIG. 3
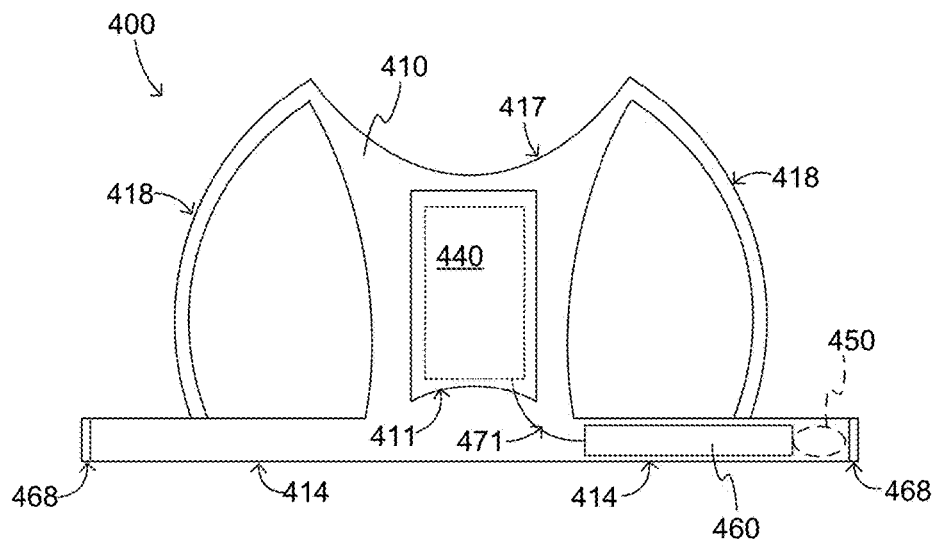
FIG. 4   *WEARABLE MEDICAL SYSTEM*

WEARABLE MEDICAL SYSTEM WITH STRETCH-CABLE ASSEMBLY

CROSS REFERENCE TO RELATED PATENT APPLICATIONS

This patent application is a divisional of U.S. patent application Ser. No. 14/510,081, filed on Oct. 8, 2014, which in turn claims priority from U.S. Provisional Patent Application Ser. No. 61/989,464, filed on May 6, 2014, titled: "ELASTICALLY EXPANDABLE WIRING ASSEMBLY FOR WEARABLE MEDICAL DEVICE", the disclosure of which is hereby incorporated by reference for all purposes.

BACKGROUND

People increasingly wear wearable medical systems (WMS), some of which contain electronics and cables. A challenge is in designing the length of cables that will be partly around the body of the person who wears the WMS, because there are variations. First, not all those who wear WMSs are of the same size. Second, even a single person's size can change, both gradually as that person may lose or gain weight, and quickly as the person moves and even breathes.

For designing the length of the cables, there are competing considerations. On the one hand, the cable should have enough slack, because if there is no slack or the slack is lost, the connections of the cable alone can become pressure points on the person's body, creating discomfort. Moreover, for wearable medical systems that attain low electrical noise and high signal quality, such a cable may need to be a shielded coaxial cable, which makes it thicker and more prone to create pressure points. On the other hand, if the cable has too much slack, it can interfere with the person's movement, and it can become tangled with their garments or other articles of clothing or even other components of the system itself.

BRIEF SUMMARY

The present description gives instances of Wearable Medical Systems (WMSs) and related methods, the use of which may help overcome problems and limitations of the prior art.

In one embodiment, a support structure is configured to be worn by a person. An electronics module, a cable assembly, and at least one electrode can be configured to be coupled to the support structure. The cable assembly includes a base member and a cable coupled to the base member. The support structure can be dimensioned relative to the person's body to be worn with tension, and be resiliently stretched under the tension. The stretching of the support structure can stretch the base member of the cable assembly, thus increasing the effective length of the cable.

An advantage over the prior art is that, while different effective cable lengths may be accommodated, there is less or even no slack. Indeed, different effective cable lengths can be achieved by how much the cable assembly can be stretched. Moreover, the cable assembly can absorb some or even all of the cable slack, and thus not interfere with the person's movement.

These and other features and advantages of this description will become more readily apparent from the Detailed Description, which proceeds with reference to the associated drawings in which:

BRIEF DESCRIPTION OF THE DRAWINGS

FIG. 1 is a diagram of sample components of a wearable medical system (WMS) according to embodiments.

FIG. 2 is a diagram illustrating two views of a sample embodiment of a cable assembly such as a cable assembly of the components of FIG. 1 according to embodiments.

FIG. 3 is a diagram illustrating a sample configuration of components of a WMS according to embodiments.

FIG. 4 is a diagram of a sample WMS according to embodiments.

DETAILED DESCRIPTION

Figure 5:
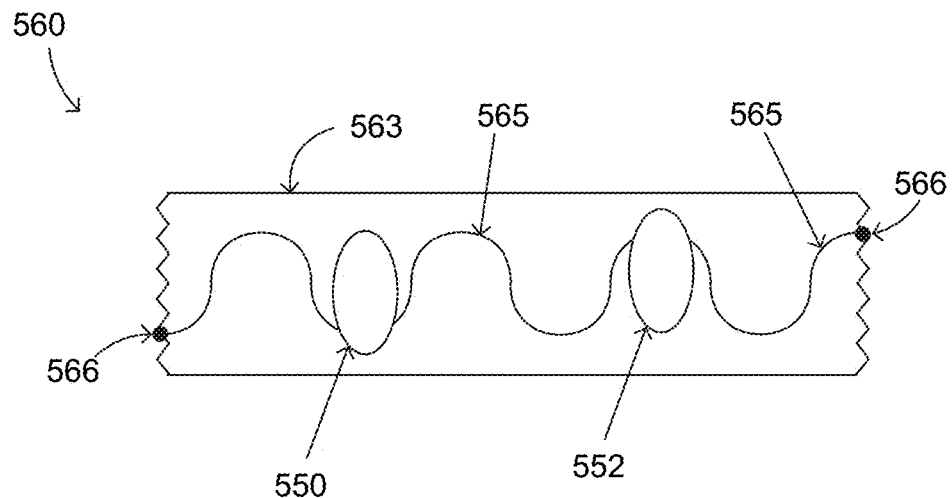
FIG. 5 is a view of a sample portion of a cable assembly of a WMS according to embodiments.

As has been mentioned, the present description is about Wearable Medical Systems (WMSs) and related methods. Embodiments are now described in more detail.

FIG. 1 is a diagram of sample components 100 of a wearable medical system (WMS) according to embodiments. Components 100 are intended to be worn by a person 182. Person 182 may be healthy, and the WMS is intended to track their health; in other instances, however, person 182 can be a patient, and be referred to as patient 182.

Only a section of the body of person 182 is shown, but it is understood that components 100 can be worn on the torso, the arm, the leg, the head, etc. of person 182. One or more of components 100 can be put directly on person 182, as will be seen later in more detail.

Components 100 of a Wearable Medical Systems (WMS) are now described in more detail.

Components 100 include a support structure 110, which is shown abstractly in FIG. 1. Support structure 110 can be configured to be worn by person 182. Support structure 110 can thus be implemented as described in this document, and in addition be part of a belt, a harness, a garment, a holster, and so on. Support structure 110 can be dimensioned relative to the body of person 182 to be so worn with tension 112. In other words, in some embodiments at some times support structure 110 does not fit person 182 everywhere loosely, but is worn with non-zero tension 112, i.e. tension of non-zero magnitude that can gently squeeze person 182. The tension may ensure that any electrodes make good electrical contact with person 182. In embodiments when support structure 110 is so worn with the tension, it is stretched under the tension; preferably it is being stretched resiliently, which means that it regains its shape when the tension is removed. The resilience is accomplished as described later in this document. The tension can be removed when person 182 removes support structure 110 from his body.

In some embodiments, the wearable medical system includes a single support structure 110. In other embodiments, additional support structures are provided, such as support structure 119.

Components 100 also include an electronics module 140. Electronics module 140 can be a part of the wearable medical system that monitors physiological signals of person 182, makes determinations from these signals, communicates with the person or with entities remote from the person, and so on. In embodiments where the WMS is a wearable defibrillator, electronics module 140 may include an energy storage module, which is configured to store electrical energy.

Electronics module 140 can be configured to be coupled to support structure 110. Coupling can be permanent, such as attaching. In some embodiments, however, electronics module 140 can be coupled to and uncoupled from support structure 110, either by the manufacturer, or by person 182, and so on.

In some embodiments, the system includes a single electronics module 140. In other embodiments additional electronics modules are provided, such as electronics module 149. If provided, electronics module 149 may communicate with electronics module 140, be electrically coupled to it, and so on. If provided, electronics module 149 can be configured to be coupled to support structure 110, or to support structure 119 if provided, and so on.

Components 100 additionally include an electrode 150, perhaps an additional electrode 152, and possibly even other electrodes (not shown). Electrode 150 can be configured to be physically coupled to the skin of person 182, when support structure 110 is worn as described above. As will be seen, a number of configurations of components 100 may accomplish this. For example, one or more of the electrodes may be attached to one component, while other electrodes may be attached to another component, only be coupled to it, and so on. In particular, electrode 150 could be physically attached to support structure 110, for example by being constructed permanently into it, into a pocket, etc. Moreover, electrode 150 could be coupled to support structure 110, but not be permanently physically attached to it. For instance, if the WMS is a wearable defibrillator, one or more ECG electrodes could be physically attached to support structure 110, while the defibrillation electrodes could be removable.

In embodiments, support structure 110 can ensure that electrode 150 is coupled to the appropriate place on the skin of person 182, which can be facilitated by support structure 110 being under nonzero tension 112. Electrode 150 can be coupled to the skin of person 182 by contacting the skin directly, or indirectly over clothing, depending on whether the electrodes are dry or not, etc. Even when physically coupled to the skin over clothing, some electrodes can achieve electrical coupling with the person's skin through the clothing.

Components 100 further include a cable assembly 160, which can also be called stretch-cable assembly. Cable assembly 160 can be made in a number of ways according to embodiments. In some embodiments, cable assembly 160 includes a base member and a cable coupled to the base member, neither of which is shown individually in FIG. 1. Moreover, components 100 may include a cloth guard (not shown). At least a portion of cable assembly 160 can be within the cloth guard. Details of a cable assembly are now described by reference to an example.

FIG. 2 is a diagram illustrating two views 261, 262 of a sample cable assembly 260. Cable assembly 260 could be cable assembly 160 of FIG. 1.

Referring to view 261, cable assembly 260 includes a base member 263, which is substantially elongate along a main direction 201. Two securing mechanisms 268 are optionally included at ends of base member 263, which can be used for coupling as will be described later on.

Cable assembly 260 also includes a cable 265. In the example of FIG. 2, cable 265 terminates in nodes 266.

Cable 265 can be coupled to base member 263, preferably at the time of manufacture. Cable 265 can be arranged substantially along main direction 201 with respect to base member 263. In the example of FIG. 2, cable 265 is arranged in a substantially serpentine manner with respect to main direction 201. Other manners are also possible, for example helical, combination, and so on. Helical is not preferred, however, because it requires more cable for spanning the same distance between nodes 266, plus cable portions could experience needless friction against each other.

Base member 263 can be configured to be coupled to and uncoupled from a support structure, such as support structure 110 of FIG. 1. This coupling and uncoupling can be performed by person 182 manipulating securing mechanisms 268 that can be shaped appropriately like hooks, buttons, clasps, contacts, etc.

When base member 263 becomes coupled to a support structure and the support structure is worn by a person as described above, then a nonzero tension (such as tension 112 of support structure 110) may cause a tension 259 to be applied to base member 263 of cable assembly 260. In FIG. 2, this tension in base member 263 is illustrated view 262. Due to tension 259, base member 263 and cable 265 become stretched along main direction 201. The stretching is illustrated by transitioning from view 261 to view 262 of cable assembly 260. In embodiments, base member 263 can be stretched resiliently by a certain amount, which means that when tension 259 is released, cable assembly 260 returns from view 262 to view 261.

It will be appreciated that the stretching of base member 263 increases its length by an amount shown by arrow 269. In some embodiments, the stretching is by at least 4% along main direction 201. Stretching thus increases the length of cable assembly 260, the distance between nodes 266, and thus the effective length of cable 264.

Returning to FIG. 1, the base member (not shown separately) of cable assembly 160 can become coupled to support structure 110, and support structure 110 can be worn by person 182 as above. When this happens, in some embodiments electronics module 140 becomes coupled electrically with the skin of person 182 via the cable (not shown separately) of cable assembly 160, and via electrode 150. This electrical coupling 170 is shown in FIG. 1 symbolically by a spark 170, and can be accomplished either by wires, or by components being merged, or sometimes wirelessly, and so on.

In some embodiments, cable assembly 160 can become coupled to support structure 110 by being superimposed on it, or being embedded within it, at least in part. In some embodiments, cable assembly 160 is permanently attached to support structure 110.

Electrical coupling 170 can serve many functions. In some embodiments, an ECG of person 182 is sensed for electronics module 140 from voltages in electrode 150, via the cable of cable assembly 160. In embodiments where the WMS is a wearable defibrillator, after an ECG is analyzed, the stored energy can be configured to be delivered via the cable of case assembly 160 and via electrode 150 to the skin of person 182.

The system of FIG. 1 has been described generally. Many sample configurations are now described, for how components 100 could operate with each other.

FIG. 3 is a diagram illustrating a sample configuration of components 300 of a WMS, intended for a person 382. Components 300 include a support structure 310, an electronics module 340, an electrode 350 and a cable assembly 360, each of which could be an embodiment of a corresponding element in FIG. 1.

In some embodiments, support structure 310 includes an electronics pocket 311. Electronics module 340 can be configured to be coupled to support structure 310 by being inserted in electronics pocket 311. There are a number of embodiments for an electronics pocket. In the example of FIG. 3, pocket 311 has an opening that faces away from person 382. In other embodiments, the opening can be on the side facing the person, and so on. Pocket 311 can be shallow, or deep enough to receive the entire electronics module 340, and even have a flap that shuts afterwards.

In some embodiments, support structure 310 includes a resiliently stretchable portion 314. Portion 314 may be made out of fabric that includes elastic materials, elastic bands and the like. This way, when support structure 310 is worn by person 382 with tension 312, stretchable portion 314 may be extended under tension 312.

In addition, support structure 310 can have coupling mechanisms 368 for being secured around a member of the body of person 382. The distance between coupling mechanisms 368 can be part of dimensioning support structure 310 relative to the body of person 382, so that it is worn with nonzero tension 312.

In some embodiments, support structure 310 includes attachment points 316, 317. These can include structures that are custom made to cooperate with securing mechanisms 368, or simply be locations to which securing mechanisms 368 can be attached, when cable assembly 360 is coupled to support structure 310.

In some embodiments, cable assembly 360 includes a resiliently stretchable portion 364. Examples will be seen later in this document. In the example of FIG. 2, the entire base member 263 is stretchable. This way, when portion 314 of support structure 310 is extended under tension 312, it can create tension 359 in cable assembly 360, and thus stretchable portion 364 may be extended under tension 359.

In some embodiments, support structure 310 includes an electrode pocket 315. Electrode 350 can be configured to be coupled to support structure 310 by being inserted in electrode pocket 315. There are a number of embodiments for an electrode pocket. In the example of FIG. 3, pocket 315 has an opening that faces towards person 382. In other embodiments, the opening can be on the other side. In some embodiments no pocket is provided for the electrode. Sometimes a buttonhole is provided, as is described later in this document.

As with FIG. 1, in some embodiments of FIG. 3 electronics module 340 becomes coupled electrically with the skin of person 382 via the cable (not shown separately) of cable assembly 360, and via electrode 350. In FIG. 3, the electrical coupling between electronics module 340 and cable assembly 360 is shown by spark 371, while the electrical coupling between cable assembly 360 and electrode 350 is shown by spark 372. These electrical couplings 371, 372 can be implemented as was mentioned above for electrical coupling 170, and examples will be seen later in this document.

FIG. 4 is a diagram of a sample wearable medical system (WMS) 400. WMS 400 includes a support structure 410 in the form of a harness 410, an electronics module 440, an electrode 450 and a cable assembly 460, each of which can be an embodiment of a corresponding element in FIG. 1 or in FIG. 3. Other embodiments could be different. For example, electronics module 440 is where a posterior defibrillation electrode could be, alone or in combination with an electronics module. Cable assembly 460 could be longer. There could be more electrodes, etc.

In FIG. 4, harness 410 includes a backing 417, straps 418, and stretchable portions 414 that terminate in coupling mechanisms 468. Straps 418 may also be stretchable. Before wearing harness 410, the person may insert electronics module 440 in an electronics pocket 411, and couple cable assembly 460 over one of stretchable portions 414. The electrical coupling between electronics module 440 and cable assembly 460 is shown by a wire 471. Electrode 450 is on the other side of the same stretchable portion 414, and is electrically coupled to cable assembly 460 via a buttonhole, as will be described later in more detail.

Harness 410 can then be worn, with backing 417 on the back of a person (not shown), straps 418 passing over the shoulders, stretchable portions 414 stretched under the arms so that coupling mechanisms 468 can be brought together in front of the person's chest, and coupled to each other. Stretching stretchable portions 414 may also stretch cable assembly 460. In addition, electrode 450 will become physically coupled to the person's chest.

After wearing WMS 400 for a while, the person may do the opposite procedure. Particularly, the person may uncouple mechanisms 468, remove harness 410 from their back, and then remove electronics module 440, cable assembly 460, and electrode 450 from harness 410. The person may then wash harness 410, while transferring the other components to another harness for wearing.

WMS 400 shows only one electrode 450, but more electrodes can be included. For example, if WMS is to be a defibrillator, additional electrodes may be used. One or more electrodes may be implemented in conjunction with electronics module 440 in electronics pocket 411. Moreover, additional electrodes may be provided on the cable assembly. An example is now described.

FIG. 5 is a view of a portion of a cable assembly 560, made according to embodiments. Cable assembly 560 includes an elongate base member 563, and a cable 565. For the portion shown in FIG. 5, cable 565 ends in nodes 566. An electrode 550, and also a second electrode 552 are electrically coupled to cable 565.

For the electrical coupling, electrodes 550 and 552 may also be physically coupled to cable 565, and thus to cable assembly 560. In some embodiments, one or more of them can be coupled by suitable structures, such as mechanical contacts. It is preferred that electrical contacts are also included. For example, a WMS may include a snap contact that is both a mechanical contact and an electrical contact, and cable assembly 560 can be configured to become physically coupled with electrode 550 via the snap contact. Speaking of such, in some embodiments, cable assembly 560 can be configured to become physically coupled also with an electronics module of a WMS via such contacts.

In some embodiments, one or more of electrodes 550, 552 are attached to cable 565. An example is now described.

Figure 6:
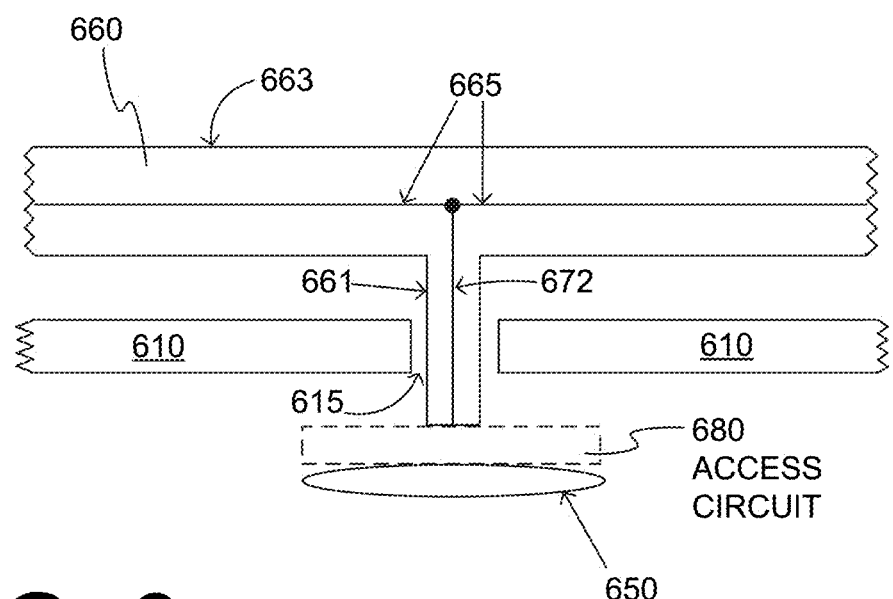
FIG. 6 is a top view of a sample portion of a section of a cable assembly and of a corresponding support structure of a WMS according to embodiments.

FIG. 6 is a top view of a portion of a cable assembly 660, and of a corresponding portion of a support structure 610, both made according to embodiments. Support structure 610 is more extended than the portion shown, and has a buttonhole 615.

Cable assembly 660 includes an elongate base member 663, and a cable 665. Cable 665 can be arranged in a serpentine or other non-linear manner as shown in previous diagrams but, in the top view of FIG. 6, cable 665 appears linear. Cable assembly 660 also includes a stub 661, which further contains a conductor 672.

In FIG. 6, an electrode 650 is attached to cable assembly 660 via stub 661. Electrode 650 can be further electrically coupled to cable 665 of cable assembly 660 via conductor 672. In some embodiments, coupling is direct. In other embodiments, the WMS additionally includes an access circuit 680. Access circuit 680 can be electrically coupled between the electronica module (not shown) and electrode 650, and more specifically between cable 665 and electrode 650. Access circuit 680 can be an electrical circuit that controls access to electrode from the electronics module, especially when a single cable is used for multiple functions, such as detecting ECG and delivering a defibrillation or pacing pulse. For this purpose, access circuit 680 may include at least a resistor, for example to prevent an electrical discharge from an undesirable electrode.

Electrode 650 may become coupled to support structure 610 by passing through buttonhole 615, similarly to buttoning a button. To enable this passing, support structure 610 can be flexible so that it can be temporarily deformed. Once electrode 650 has been passed through buttonhole 615, any stretching of support structure 610 can become tension that may stretch base member 663.

In the above described embodiments, the cable assembly included only a single cable. Such is not necessarily the case. A cable assembly according to embodiments may further include a second cable coupled to the base member, a third cable, and so on. An example is now described.

Figure 7:
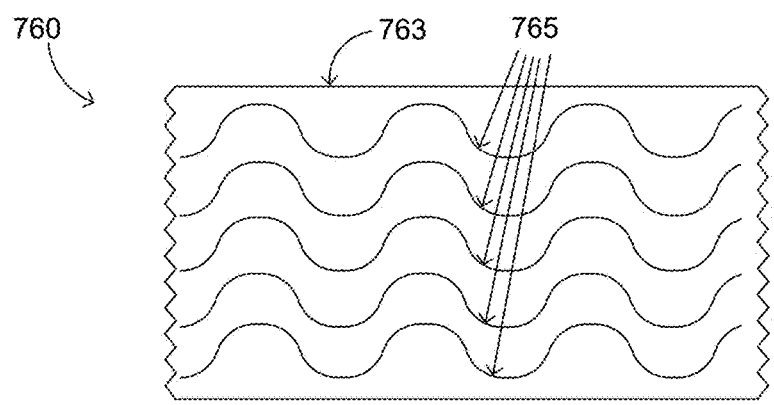
FIG. 7 is a diagram of a sample portion of a cable assembly of a WMS with multiple cables according to embodiments.

FIG. 7 is a diagram of a portion of a cable assembly 760, made according to embodiments. Cable assembly 760 includes an elongate base member 763, and multiple cables 765. In embodiments like this, a WMS could further include a second electrode electrically coupled to a second one of the cables, and so on.

Embodiments such as the one of FIG. 7 ultimately permit using multiple electrodes. This can be useful for instances where it is desired to access many different points of the person's body. For example, it may be desired to obtain a lot of ECG readings. Or it may be desired to administer defibrillation shocks along different vectors, and therefore from electrodes at different points of the person's body.

In embodiments such as the one of FIG. 7, different electrodes or groups of electrodes may have their own cables, to the exclusion of one or more other electrodes. This can be useful especially when electrodes have different functions, for example receiving ECG versus delivering electric shock therapy. A challenge, however, can be that many total cables may be needed, if it is desired to have many electrodes. This challenge can be addressed by having electrodes share the cables, and be selectable as desired for operation. In such cases, the electrodes may even serve different functions. An example is now described.

Figure 8:
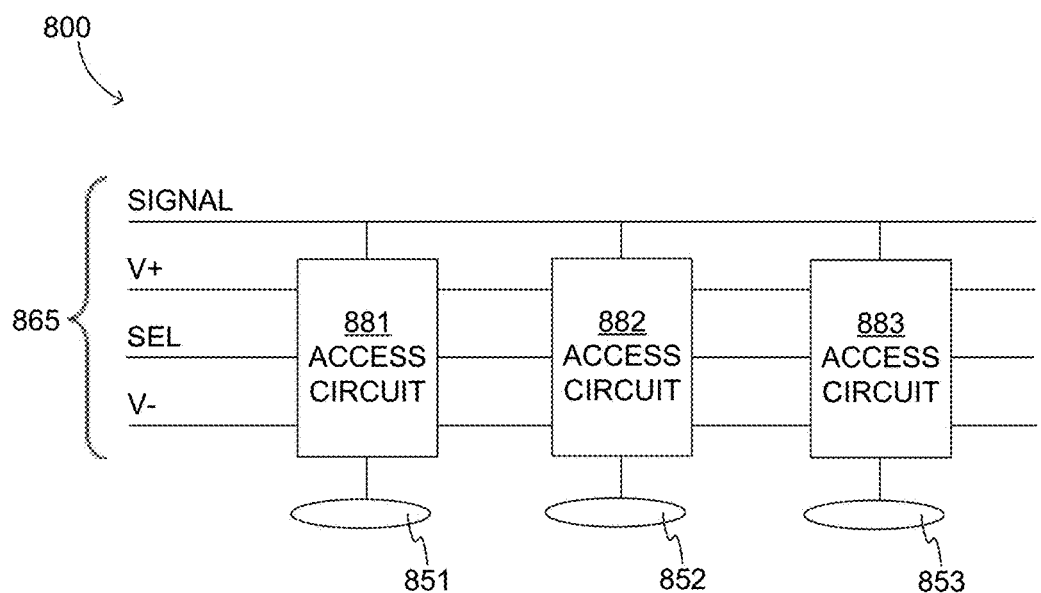
FIG. 8 is a sample electrical diagram showing how multiple electrodes of a WMS can share a few common cables of a cable assembly according to embodiments.

FIG. 8 is a sample electrical diagram 800 showing multiple electrodes 851, 852, 853 of a WMS. Four cables 865 of a cable assembly are used by electrodes 851, 852, 853. It will be apparent that more electrodes can be serviced by the same four cables 865.

In FIG. 8 one of cables 865 is labeled SIGNAL, and is what carries a sensed signal of the person, or an output pulse directed to the person, similarly with cable 265 of FIG. 2. In addition, the rest of cables 265 carry control signals.

Access circuits 881, 882, 883 are coupled between SIGNAL cable 865 and the respective electrodes 851, 852, 853. Access circuits 881, 882, 883 may affect the electrical coupling between SIGNAL cable 865 and respective electrodes 851, 852, 853; in other words, access circuits 881, 882, 883 may facilitate or hinder that electrical coupling, and in effect determine which of electrodes 851, 852, 853 get to use SIGNAL cable 865 over the other electrodes. Access circuits 881, 882, 883 may affect that electrical coupling responsive to signals V+, SEL, V− that they sense on the remaining cables 865. An example is now described.

Figure 9:
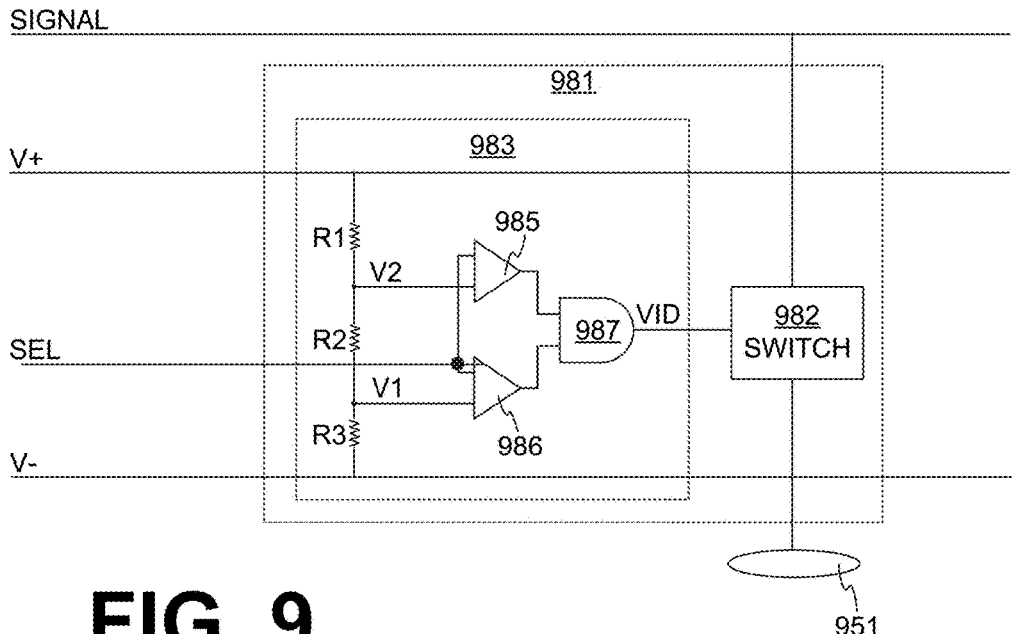
FIG. 9 is a sample electrical diagram for implementing an access circuit of FIG. 8 according to embodiments.

FIG. 9 is a sample electrical diagram for implementing an access circuit 981, which could be any one of access circuits 881, 882, 883. Access circuit 981 is electrically coupled to a SIGNAL cable and to other cables that carry signals V+, SEL, V−, all of which can be shared by other access circuits as seen in the previous diagram.

Access circuit 981 may affect the electrical coupling between the SIGNAL cable and an electrode 951. In particular, access circuit 981 includes a switch 982 that can affect the electrical coupling between the SIGNAL cable and electrode 951. Switch 982 can be current-based (transistor, etc.), voltage based (FET, etc.), and so on.

Access circuit 981 also includes a selector circuit 983, which is coupled to receive signals SEL, V+, V−. In selector circuit 983 resistors R1, R2, R3 define a resistive bridge divider that creates threshold voltages V1, V2 at appropriate nodes. Two comparators 985, 986 compare threshold voltages V1, V2 to a select voltage on the SEL cable. An AND gate 987 outputs an identification signal VID that is high when the select voltage is between threshold voltages V1, V2, and low otherwise.

Switch 982 can be operable responsive to identification signal VID that is output from selector circuit 983. When identification signal VID is high, switch 982 can be ON, facilitating the electrical coupling between the SIGNAL cable and electrode 951. When identification signal VID is low, switch 982 can be OFF, hindering the electrical coupling between the SIGNAL cable and electrode 951. Accordingly, the select voltage on the SEL cable can control the electrical coupling.

In access circuits other than access circuit 981, threshold voltages V1, V2 can be set at different values, for example by choosing resistors R1, R2, R3 having different values. Accordingly, a select voltage on the SEL cable that facilitates electrical coupling for access circuit 981 can concurrently hinder electrical coupling for another of the access circuits. In this example, the value of the select voltage can be between the values of V+ and V−. In addition, some circuits can be selected in groups, and so on. Of course, different circuits are possible. In addition, the same, similar, or other appropriate access circuits can be implemented in all other embodiments in view of the present description.

Figure 10:
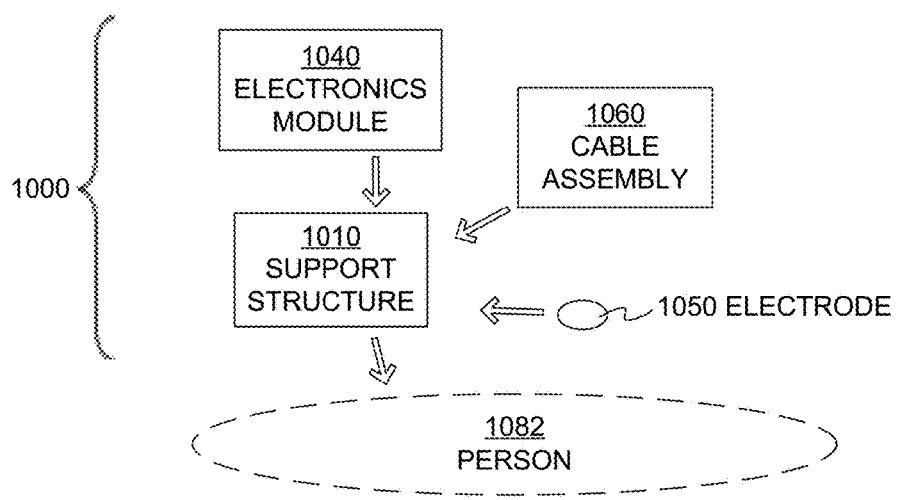
FIG. 10 is a diagram illustrating a sample configuration of components of a WMS according to embodiments.

FIG. 10 is a diagram illustrating a sample configuration of components 1000 of a WMS, intended for a person 1082. Components 1000 include a support structure 1010, an electronics module 1040, an electrode 1050 and a cable assembly 1060, each of which can be an embodiment of a corresponding element in FIG. 1. In the configuration of FIG. 10, electronics module 1040, electrode 1050 and cable assembly 1060 can be independently coupled to support structure 1010 for operation. Then these components may have to be coupled together, for forming electrical connections as mentioned previously. Then they can be uncoupled from support structure 1010, for example to be used with another support structure while support structure 1010 is washed, and so on.

Figure 11:
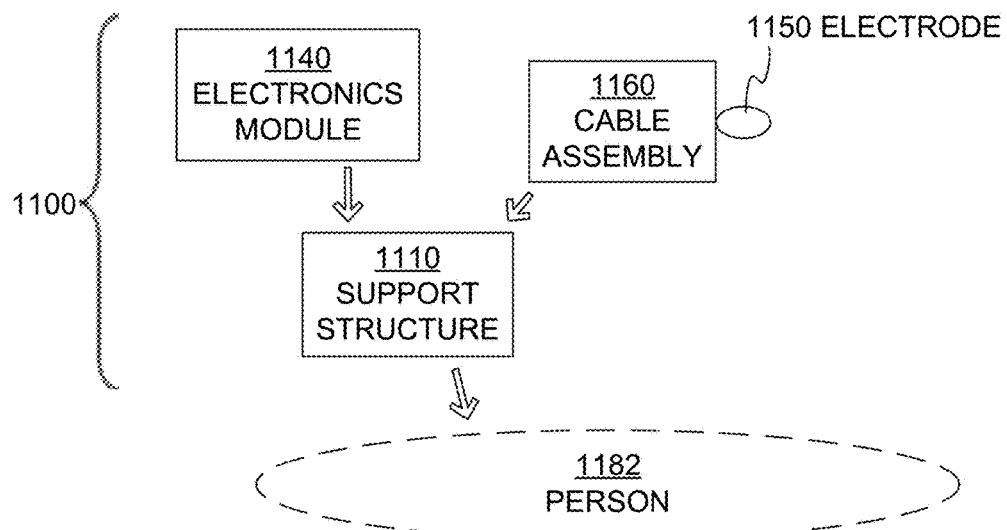
FIG. 11 is a diagram illustrating a sample configuration of components of a WMS according to embodiments.

FIG. 11 is a diagram illustrating a sample configuration of components 1100 of a WMS, intended for a person 1182. Components 1100 include a support structure 1110, an electronics module 1140, an electrode 1150 and a cable assembly 1160, each of which can be an embodiment of a corresponding element in FIG. 1. In the configuration of FIG. 11, electrode 1150 is attached to a cable (not shown) of cable assembly 1160, and therefore electrode 1150 is attached to cable assembly 1160. Accordingly, there may be less coupling needed to be done by person 1182 than person 1082 in FIG. 10.

Figure 12:
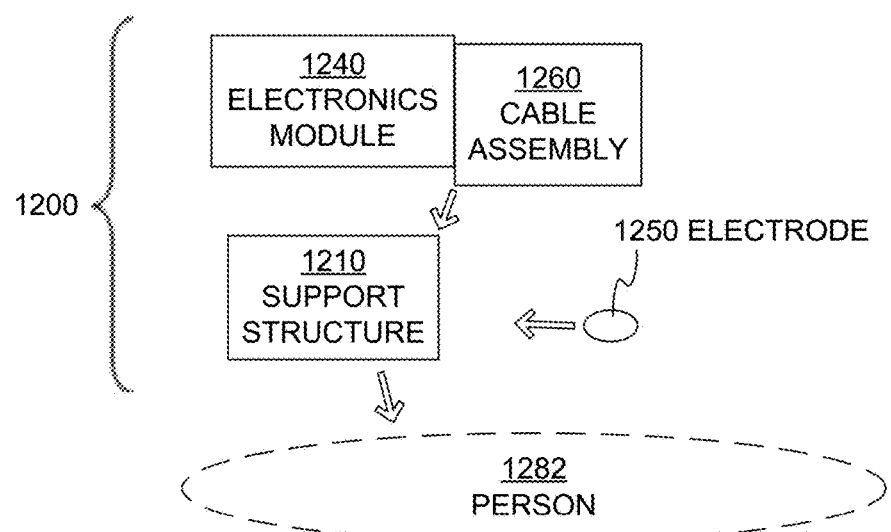
FIG. 12 is a diagram illustrating a sample configuration of components of a WMS according to embodiments.

FIG. 12 is a diagram illustrating a sample configuration of components 1200 of a WMS, intended for a person 1282. Components 1200 include a support structure 1210, an electronics module 1240, an electrode 1250 and a cable assembly 1260, each of which can be an embodiment of a corresponding element in FIG. 1. In the configuration of FIG. 12, electronics module 1240 is attached to a cable (not shown) of cable assembly 1260, and therefore electronics module 1240 is attached to cable assembly 1260. Accordingly, there may be less coupling needed to be done by person 1282 than person 1082 in FIG. 10.

Figure 13:
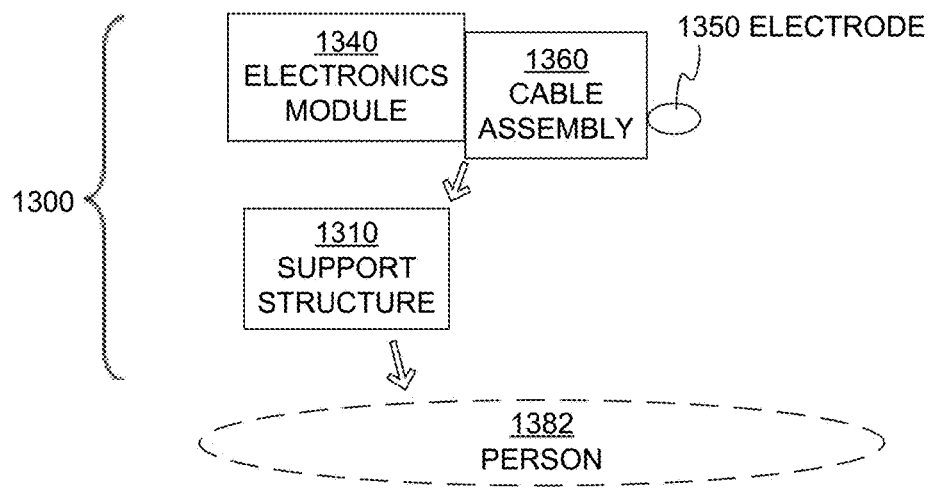
FIG. 13 is a diagram illustrating a sample configuration of components of a WMS according to embodiments.

FIG. 13 is a diagram illustrating a sample configuration of components 1300 of a WMS, intended for a person 1382. Components 1300 include a support structure 1310, an electronics module 1340, an electrode 1350 and a cable assembly 1360, each of which can be an embodiment of a corresponding element in FIG. 1. In the configuration of FIG. 13, electronics module 1340 and electrode 1350 are attached to a cable (not shown) of cable assembly 1360, and therefore electronics module 1340 and electrode 1350 are attached to cable assembly 1360. Accordingly, there may be less coupling needed to be done by person 1382 than person 1082 in FIG. 10.

The cable assembly is now described in more detail. In embodiments, the base member includes an elastic material, which can be stretched. The cable is coupled to the cable assembly with some slack, to accommodate the stretching.

Figure 14:
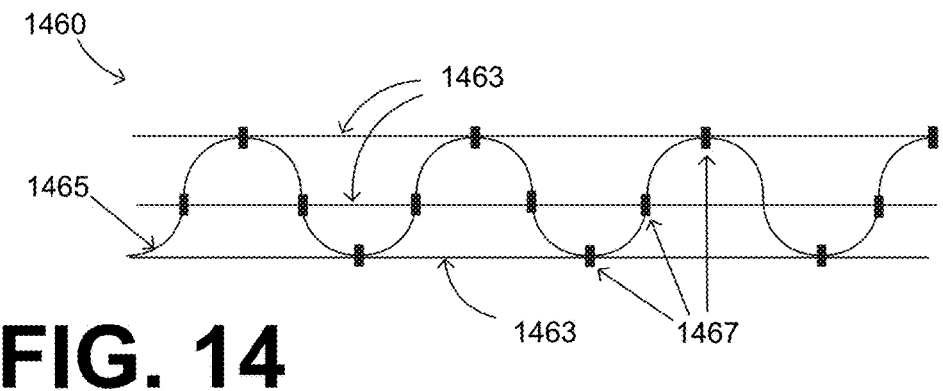
FIG. 14 is a diagram of sample elements of a portion of a cable assembly of a WMS according to embodiments.

FIG. 14 is a diagram of sample elements of a portion 1460 of a cable assembly that has a cable 1465. The base member includes at least one, and preferably three strands 1463 of an elastic material. More than one strand 1463 will help prevent tangling of cable 1465 better. Cable 1465 is attached to strands 1463 at a plurality of points, using attachment implements 1467. Attachment implements 1467 can be implemented in any number of ways, such as by sewing, heat molding, and so on.

Figure 15:
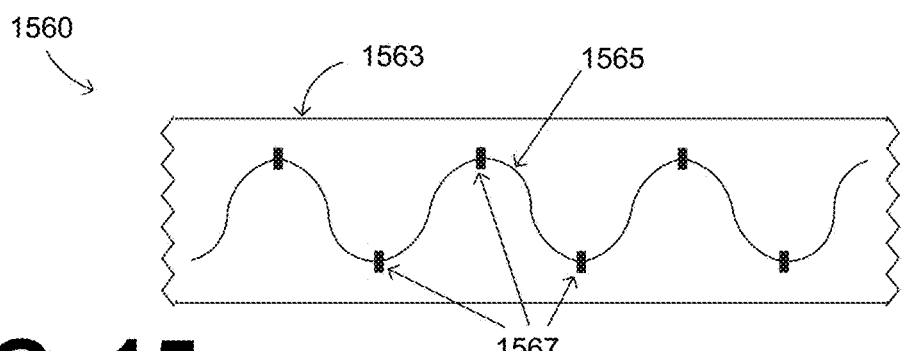
FIG. 15 is a diagram of a sample portion of a cable assembly of a WMS according to embodiments.

FIG. 15 is a diagram of a sample portion 1560 of a cable assembly, which has a base member 1563 and a cable 1565. Base member 1563 may include a fabric, such as a stretchable fabric. Or it may include an elastomer, such as urethane or a silicone sheet. In the example of FIG. 15, attachment implements 1567 attach cable 1565 to base member 1563.

In some embodiments a base member may be implemented as a single sheet, or layer, to which the cable can be attached. In other embodiments, at least a portion of the cable is inside the base member. For example, the base member can include two sheets, or layers, of material, which sandwich the cable and are pressed against each other. The sheets, or layers, can be as described above for base member 1563, and can be solid.

Moreover, an additional structure between the two sheets of material can hold the cable in place. If two layers are provided, the additional structure can be an intermediate structure that serves as an intermediate layer. Such an intermediate structure can be advantageously made via a film, from a stretchable material such as an elastomer. Such an intermediate structure can further be adhesive, for holding also the other two layers together. The additional structure can first hold the cable in place at a desired configuration such as the serpentine configuration during manufacture, before the two sheets of material become pressed against each other. The additional structure can first hold the cable at the desired configuration by having openings, through which the cable can be routed. An advantage is that these openings permit reducing the force needed to elastically stretch the cable assembly. In other embodiments, the cable can be adhered to the intermediate structure. An example is now described.

Figure 16:
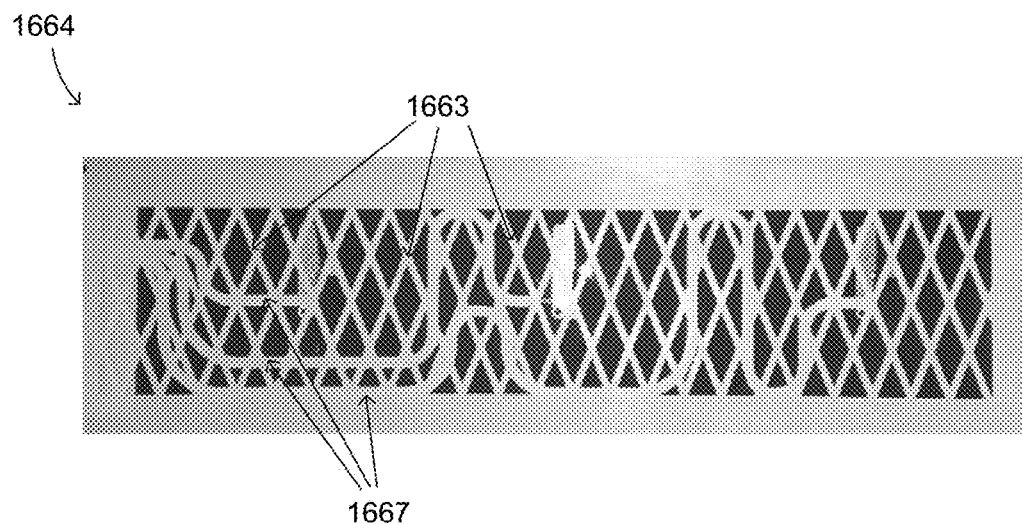
FIG. 16 shows a sample intermediate structure of a cable assembly of a WMS according to embodiments.

FIG. 16 shows an additional structure 1664 that could be placed between the two sheets of material to hold the cable in place, as described above. If two layers are provided, additional structure 1664 can be an intermediate structure that serves as an intermediate layer. In the example of FIG. 16, additional structure 1664 is shown against a dark background. Additional structure 1664 forms a lattice 1663, which is diamond shaped. Lattice 1663 of course defines openings, which could be the openings described in the previous paragraph. In the example of FIG. 16, however, additional structure 1664 forms three cable traces 1667 superimposed on lattice 1663. The cable can be attached to additional structure 1664 along one of cable traces 1667. In this example, looking from left to right, three cable traces 1667 start, and each terminates at a point where an electrode can be. Cable traces 1667 are not necessarily stretchable where they are horizontal, and they can be horizontal at places where an electronics module would prevent stretching anyway.

Figure 17:
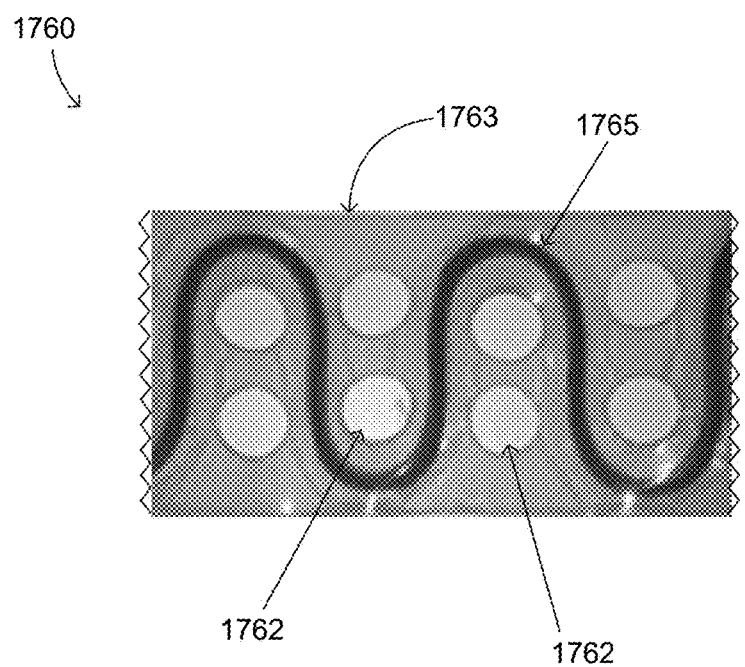
FIG. 17 shows a sample portion of a cable assembly of a WMS according to embodiments.

FIG. 17 shows a sample portion 1760 of a cable assembly, which has a base member 1763 and a cable 1765. Base member 1763 may be made by two sheets of an elastomer material that are pressed together and sandwich cable 1765, such as described above. In the example of FIG. 17, base member 1763 includes at least two perforations 1762. Cable 1765 passes between perforations 1762, while sandwiched between the two sheets.

Figure 18:
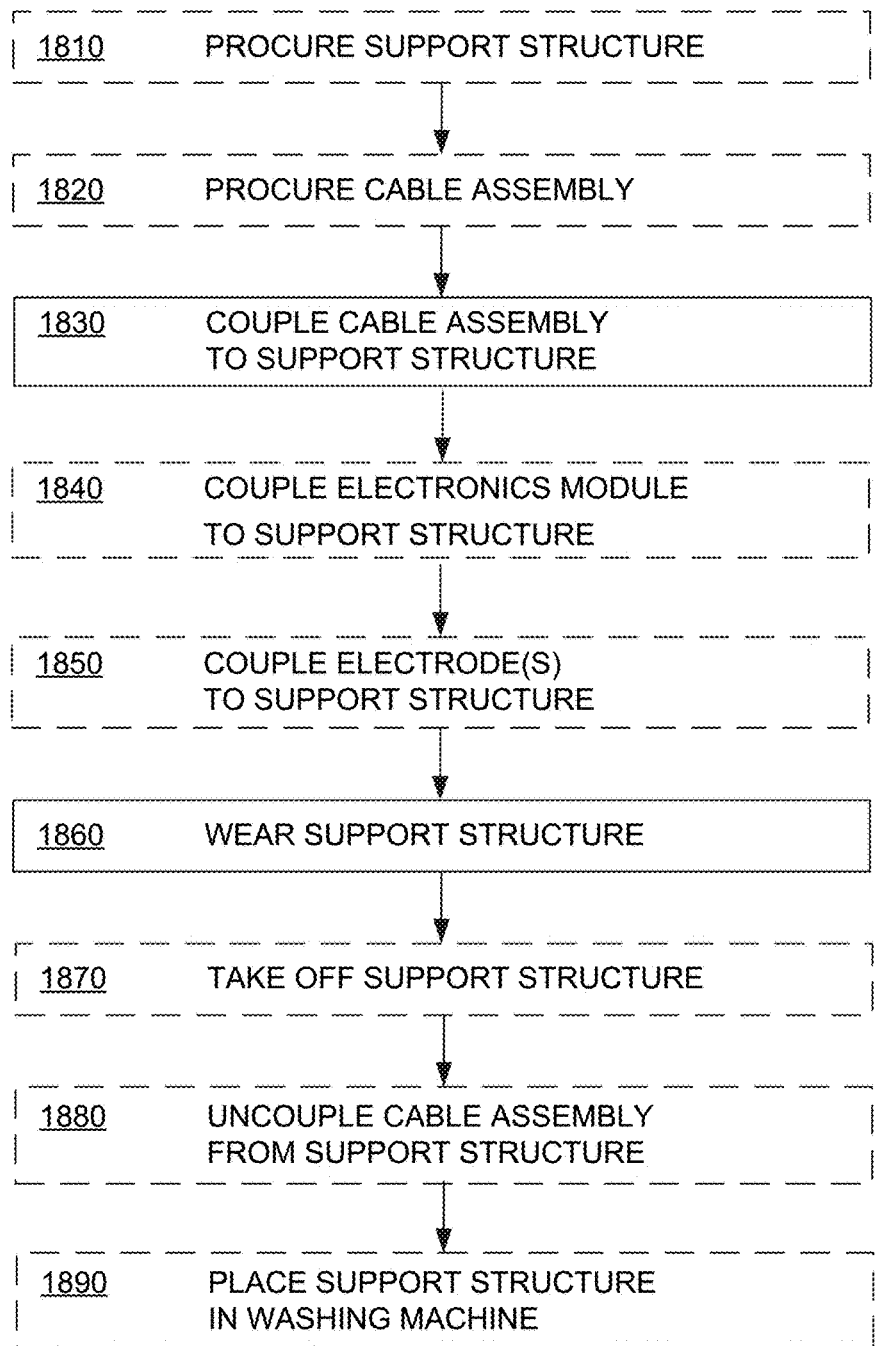
FIG. 18 is a flowchart for illustrating methods according to embodiments.

FIG. 18 shows a flowchart 1800 for describing methods according to embodiments. The methods of flowchart 1800 may also be practiced by using embodiments described elsewhere in this document.

According to an optional operation 1810, a support structure is procured. According to another optional operation 1820, a cable assembly is procured. According to another operation 1830, the cable assembly is coupled to the support structure.

According to another, optional operation 1840, an electronics module is coupled to the support structure. According to another, optional operation 1850, one or more electrodes are coupled to the support structure. The electrode can be connected to the cable assembly; in fact, the support structure may include a buttonhole, in which case coupling can be performed by passing the electrode through the buttonhole. Or, the electrode can be procured separately, and then be electrically coupled to the cable assembly.

According to another operation 1860, the support structure is worn. The support structure can be worn with nonzero tension, which stretches the support structure. The support structure being stretched causes the coupled cable assembly to also be stretched by at least 4% along a main direction.

According to another, optional operation 1870, the support structure is taken off, preferably after wearing it for a while. According to another, optional operation 1880, the cable assembly and other components may be uncoupled from the support structure. According to another, optional operation 1890, the support structure may be placed in a washing machine.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in any number of ways, as will be apparent to a person skilled in the art after reviewing the present disclosure, beyond any examples shown in this document.

The following claims define certain combinations and subcombinations of elements, features and steps or operations, which are regarded as novel and non-obvious. Additional claims for other such combinations and subcombinations may be presented in this or a related document.

What is claimed is:

1. A Wearable Medical System (WMS), comprising:
   a support structure configured to be worn by a person, the support structure dimensioned relative to a body of the person to be so worn with nonzero tension, the support structure being resiliently stretched under the tension when so worn;
   an electronics module configured to be coupled to the support structure;
   a base member that is substantially elongate along a main direction, the base member configured to be coupled to and uncoupled from the support structure, the base member being resiliently stretched by at least 4% along the main direction when the base member is so coupled and the support structure is so worn;
   a cable coupled to the base member, the cable arranged substantially along the main direction with respect to the base member the cable including two nodes;
   a first electrode configured to be physically coupled to a skin of the person when the support structure is so worn, the first electrode being electrically coupled to the cable between the two nodes; and
   a second electrode electrically coupled to the cable between the two nodes, and
   in which the electronics module becomes coupled electrically with the skin of the person via the cable and via the first electrode when the base member is coupled to the support structure and the support structure is so worn.

2. The WMS of claim 1, in which
   the electronics module includes an energy storage module configured to store electrical energy, and
   the energy is configured to be delivered via the cable and via the first electrode to the person's skin when the support structure is so worn and the base member is coupled to the support structure.

3. The WMS of claim 1, in which
   the first electrode is physically attached to the support structure.

4. The WMS of claim 1, in which
   the first electrode is physically attached to the support structure, and
   the second electrode can be coupled to the support structure but is not permanently physically attached to the support structure.

5. The WMS of claim 1, in which
   the cable is arranged in a substantially serpentine manner with respect to the main direction.

6. The WMS of claim 1, in which
   the support structure includes an electronics pocket, and
   the electronics module is configured to be coupled to the support structure by being inserted in the electronics pocket.

7. The WMS of claim 1, in which
   the support structure includes an electrode pocket, and
   the first electrode is configured to be coupled to the support structure by being received in the electrode pocket.

8. The WMS of claim 1, in which
   the first electrode and the second electrode are attached to the cable.

9. The WMS of claim 1, further comprising:
   a mechanical contact, and in which the cable is configured to become coupled physically coupled with the first electrode or with the electronics module via the mechanical contact.

10. The WMS of claim 9, in which
the mechanical contact is a snap contact.

11. The WMS of claim 1, further comprising:
an access circuit coupled between the electronics module and the first electrode.

12. The WMS of claim 1, further comprising:
an access circuit coupled between the cable and the first electrode.

13. The WMS of claim 12, in which
the access circuit includes a resistor.

14. The WMS of claim 1, further comprising:
a second cable coupled to the base member.

15. The WMS of claim 14, further comprising:
an access circuit coupled between the cable and the first electrode.

16. The WMS of claim 1, in which
the first electrode is attached to the cable.

17. The WMS of claim 1, in which
the electronics module is attached to the cable.

18. The WMS of claim 17, in which
the first electrode is attached to the cable.

19. The WMS of claim 1, in which
the base member includes at least one of a fabric, an elastomer, and an elastic material.

20. The WMS of claim 1, in which
the base member includes a strand of an elastic material, and
the cable is attached to the strand at a plurality of points.

21. The WMS of claim 1, further comprising:
attachment implements that attach the cable to the base member.

22. The WMS of claim 1, in which
at least a portion of the cable is inside the base member.

23. The WMS of claim 1, in which
the base member includes two sheets of material sandwiching the cable and pressed against each other.

24. The WMS of claim 23, in which
the base member further includes an additional structure between the two sheets of material.

25. The WMS of claim 24, in which
the additional structure is made of film.

26. The WMS of claim 24, in which
the additional structure forms a lattice and a cable trace superimposed on the lattice, and
the cable is attached to the additional structure along the cable trace.

27. The WMS of claim 23, in which
the base member includes at least two perforations, and
the cable passes between the two perforations.

28. A Wearable Medical System (WMS), comprising:
a support structure configured to be worn by a person, the support structure dimensioned relative to a body of the person to be so worn with nonzero tension, the support structure being resiliently stretched under the tension when so worn;
an electronics module configured to be coupled to the support structure;
an electrode configured to be physically coupled to a skin of the person when the support structure is so worn;
a base member that is substantially elongate along a main direction, the base member configured to be coupled to and uncoupled from the support structure, the base member being resiliently stretched by at least 4% along the main direction when the base member is so coupled and the support structure is so worn;
a first cable coupled to the base member, the first cable arranged substantially along the main direction with respect to the base member; and
an access circuit coupled between the electronics module and the electrode, or coupled between the first cable and the electrode, and
in which the electronics module becomes coupled electrically with the skin of the person via the first cable and via the electrode when the base member is coupled to the support structure and the support structure is so worn.

29. The WMS of claim 28, in which
the electronics module includes an energy storage module configured to store electrical energy, and
the energy is configured to be delivered via the first cable and via the electrode to the person's skin when the support structure is so worn and the base member is coupled to the support structure.

30. The WMS of claim 28, in which
the support structure includes an electrode pocket, and
the electrode is configured to be coupled to the support structure by being received in the electrode pocket.

31. The WMS of claim 28, in which
the electrode is attached to the first cable.

32. The WMS of claim 28, in which
the access circuit includes a resistor.

33. The WMS of claim 28, in which
the base member includes at least one of a fabric, an elastomer, and an elastic material.

34. The WMS of claim 28, further comprising:
a second cable coupled to the base member, and
in which the access circuit is coupled between the first cable and the electrode, and
the access circuit affects the electrical coupling between the first cable and the electrode responsive to a signal on the second cable.

35. The WMS of claim 34, in which
the access circuit includes a switch that affects the electrical coupling between the first cable and the electrode,
the access circuit also includes a selector circuit coupled to receive the signal on the second cable, and
the switch is operable responsive to an output of the selector circuit.

* * * * *

UNITED STATES PATENT AND TRADEMARK OFFICE
CERTIFICATE OF CORRECTION

PATENT NO. : 9,700,225 B2
APPLICATION NO. : 15/192588
DATED : July 11, 2017
INVENTOR(S) : Buchanan et al.

Page 1 of 1

It is certified that error appears in the above-identified patent and that said Letters Patent is hereby corrected as shown below:

In the Specification

In Column 7, Line 28, Delete "eletronica" and insert -- eletronics --, therefor.

Signed and Sealed this
Thirty-first Day of October, 2017

Joseph Matal
*Performing the Functions and Duties of the
Under Secretary of Commerce for Intellectual Property and
Director of the United States Patent and Trademark Office*